(12) United States Patent
Sweet et al.

(10) Patent No.: US 10,351,285 B2
(45) Date of Patent: Jul. 16, 2019

(54) SYSTEMS AND METHODS FOR AUTOMATICALLY VERIFYING PACKAGING OF SOLID PHARMACEUTICALS VIA ROBOTIC TECHNOLOGY ACCORDING TO PATIENT PRESCRIPTION DATA

(71) Applicant: MTS Medication Technologies, Inc., St. Petersburg, FL (US)

(72) Inventors: Mark Sweet, St. Petersburg, FL (US); Edward D Kames, Tarpon Springs, FL (US); Heather Gileta, St. Petersburg, IL (US); Robert Barrett, Treasure Island, FL (US); Alan Kraemer, Seminole, FL (US)

(73) Assignee: MTS Medication Technologies, Inc., St. Petersburg, FL (US)

( * ) Notice: Subject to any disclaimer, the term of this patent is extended or adjusted under 35 U.S.C. 154(b) by 422 days.

(21) Appl. No.: 14/532,853

(22) Filed: Nov. 4, 2014

(65) Prior Publication Data
US 2016/0122060 A1    May 5, 2016

(51) Int. Cl.
*B65B 57/10*    (2006.01)
*B65B 35/18*    (2006.01)
(Continued)

(52) U.S. Cl.
CPC ............. *B65B 57/10* (2013.01); *B65B 5/105* (2013.01); *B65B 5/12* (2013.01); *B65B 35/18* (2013.01);
(Continued)

(58) Field of Classification Search
CPC ......... B65B 5/105; B65B 5/103; B65B 37/04; B65B 5/12; B65B 35/18; B65B 5/108;
(Continued)

(56) References Cited

U.S. PATENT DOCUMENTS 2,117,685 A    5/1938   Smith, Jr.
2,177,863 A    10/1939  Cadden
(Continued)

FOREIGN PATENT DOCUMENTS

CN    107430505       12/2017
EP    2 062 822 A1    5/2009
(Continued)

OTHER PUBLICATIONS

International Patent Application No. PCT/US15/58875, International Preliminary Report on Patentability dated May 9, 2017, 7 pages.
(Continued)

*Primary Examiner* — Alexander M Valvis
*Assistant Examiner* — Eduardo R Ferrero
(74) *Attorney, Agent, or Firm* — Kilpatrick Townsend & Stockton LLP (57) ABSTRACT

Robotic pick-and-place automation is used to transfer oral solid pharmaceuticals from moveable trays or canisters. Sensors are used to verify that the pharmaceuticals have been properly placed in the desired pharmaceutical locations precisely according to the patient prescription data. A pharmacist places pharmaceutical products within dispensing trays or canisters to present the pharmaceutical products for picking and placing via the robotic pick-and-place machinery. Once the canister or tray is located adjacent the pick-and-place device, a sensor or imaging unit associated with the pick-and-place device verifies that the pharmaceutical product the size, shape, and/or color of an expected pharmaceutical product that is to be placed within the packaging material in accordance with patient prescription data stored by a computer associated with the system. Sensors verify that each individual pharmaceutical specified by a patient
(Continued)

prescription have been deposited into each specified location strictly in accordance with the patient prescription data.

16 Claims, 4 Drawing Sheets

(51) Int. Cl.
| | | |
|---|---|---|
| *G06F 19/00* | (2018.01) | |
| *B65B 39/00* | (2006.01) | |
| *B65B 5/10* | (2006.01) | |
| *B65B 5/12* | (2006.01) | |
| *B65B 61/26* | (2006.01) | |
| *B65G 47/91* | (2006.01) | |
| *B25J 15/06* | (2006.01) | |

(52) U.S. Cl.
CPC ........ B65B 39/007 (2013.01); G06F 19/3462 (2013.01); *B25J 15/0616* (2013.01); *B65B 5/103* (2013.01); *B65B 5/108* (2013.01); *B65B 61/26* (2013.01); *B65G 47/917* (2013.01)

(58) Field of Classification Search
CPC ......... B65B 35/38; B65B 59/00; B65B 59/02; B65B 59/04; B25J 9/1687; B25J 15/0616; G06F 19/3462; A61J 7/0076; A61J 7/02; B65G 47/917
USPC ............................ 700/244, 259; 53/154, 237
See application file for complete search history.

(56) References Cited

U.S. PATENT DOCUMENTS

| | | | |
|---|---|---|---|
| 2,774,175 A | 12/1956 | Maddocks | |
| 2,782,966 A | 2/1957 | Wiedenmeier | |
| 3,007,595 A | 11/1961 | Remle | |
| 3,633,732 A * | 1/1972 | Russell | B65B 25/046 198/575 |
| 3,677,437 A * | 7/1972 | Haigler | G06M 7/00 221/7 |
| 3,896,968 A | 7/1975 | Pehr | |
| 3,991,908 A | 11/1976 | Thomas | |
| 4,209,114 A | 6/1980 | Wilson | |
| 4,238,902 A | 12/1980 | Holl et al. | |
| 4,301,942 A | 11/1981 | Kupperman et al. | |
| 4,616,752 A | 10/1986 | Ridgley | |
| 4,776,501 A | 10/1988 | Ostrowsky | |
| 4,809,880 A | 3/1989 | Stein | |
| 4,964,495 A | 10/1990 | Ramussen | |
| 5,408,443 A | 4/1995 | Weinberger | |
| 5,429,551 A | 7/1995 | Uecker et al. | |
| 5,484,089 A | 1/1996 | Picerno | |
| 5,524,799 A | 6/1996 | Skillin | |
| 5,852,911 A | 12/1998 | Yuyama | |
| 5,873,463 A | 2/1999 | Purcell | |
| 5,907,493 A * | 5/1999 | Boyer | G06F 19/3462 700/213 |
| 5,921,383 A | 7/1999 | Shefler et al. | |
| 6,098,241 A | 8/2000 | Wood | |
| 6,219,587 B1 * | 4/2001 | Ahlin | G06F 19/3462 700/233 |
| 6,237,804 B1 | 5/2001 | Peery | |
| 6,259,654 B1 | 7/2001 | de la Huerga | |
| 6,267,265 B1 | 7/2001 | Issa | |
| 6,370,841 B1 * | 4/2002 | Chudy | B65B 5/103 221/10 |
| 6,431,399 B2 | 8/2002 | Gabel | |
| 6,494,776 B1 | 12/2002 | Molbak | |
| 6,561,379 B1 | 5/2003 | Goh | |
| 6,574,912 B1 | 6/2003 | Johnson | |
| 6,769,228 B1 * | 8/2004 | Mahar | B65B 61/20 53/155 |
| 6,817,481 B2 | 11/2004 | Alexander | |
| 6,948,634 B2 | 9/2005 | Evans | |
| 7,080,755 B2 | 7/2006 | Handfield | |
| 7,182,105 B1 | 2/2007 | Feehan et al. | |
| 7,207,464 B2 | 4/2007 | Brenner | |
| 7,225,597 B1 | 6/2007 | Knoth | |
| 7,360,669 B2 | 4/2008 | Drajan | |
| 7,418,311 B1 | 8/2008 | Lagassey | |
| 7,438,201 B2 * | 10/2008 | Kim | B65B 5/103 221/200 |
| 7,559,436 B2 | 7/2009 | Bieger | |
| 7,783,383 B2 * | 8/2010 | Eliuk | A61J 1/20 141/1 |
| 7,848,846 B2 * | 12/2010 | Uema | G07F 11/62 221/119 |
| 7,987,628 B2 | 8/2011 | Le Laidier et al. | |
| 8,521,326 B1 | 8/2013 | Holtje | |
| 8,657,155 B2 | 2/2014 | Dwork | |
| 8,683,737 B2 | 4/2014 | Studer et al. | |
| 8,833,603 B1 | 9/2014 | Balasubramanian et al. | |
| 8,944,282 B2 | 2/2015 | Kroupa | |
| 9,073,206 B2 | 7/2015 | Carson et al. | |
| 9,238,518 B2 | 1/2016 | Luciano, Jr. et al. | |
| 9,308,149 B1 | 4/2016 | Niskey, Jr. | |
| 2001/0034202 A1 | 10/2001 | Nottingham et al. | |
| 2002/0162843 A1 | 11/2002 | Alley | |
| 2003/0196869 A1 | 10/2003 | Molbak | |
| 2004/0034447 A1 * | 2/2004 | Vollm | B65B 5/103 700/235 |
| 2005/0194391 A1 | 9/2005 | Domke et al. | |
| 2005/0263537 A1 | 12/2005 | Gerold et al. | |
| 2006/0118573 A1 | 6/2006 | Ganz et al. | |
| 2006/0138162 A1 | 6/2006 | Anderson | |
| 2006/0201333 A1 | 9/2006 | Friel, Sr. et al. | |
| 2007/0032762 A1 | 2/2007 | Vogel | |
| 2007/0113578 A1 | 5/2007 | Wu et al. | |
| 2007/0125046 A1 | 6/2007 | Siegel et al. | |
| 2007/0157548 A1 | 7/2007 | Knoth | |
| 2007/0181614 A1 | 8/2007 | Rvachov et al. | |
| 2007/0185615 A1 * | 8/2007 | Bossi | G06F 19/3462 700/244 |
| 2007/0283821 A1 | 12/2007 | May et al. | |
| 2008/0029517 A1 | 2/2008 | Briers | |
| 2008/0093372 A1 * | 4/2008 | Milton | B65B 5/103 221/13 |
| 2008/0222999 A1 * | 9/2008 | Monti | B65B 5/103 53/244 |
| 2008/0223001 A1 * | 9/2008 | Monti | B65B 5/105 53/246 |
| 2008/0271414 A1 * | 11/2008 | Yuyama | B65B 5/103 53/53 |
| 2008/0271417 A1 * | 11/2008 | Drost | B65B 5/103 53/443 |
| 2009/0056283 A1 * | 3/2009 | Monti | B65B 5/08 53/475 |
| 2009/0056825 A1 * | 3/2009 | Mertens | B65B 5/103 141/1 |
| 2009/0065525 A1 * | 3/2009 | Shen | A61J 7/0084 221/211 |
| 2009/0120042 A1 * | 5/2009 | Zieher | B65B 5/103 53/467 |
| 2009/0133362 A1 * | 5/2009 | Bentele | B65B 5/103 53/54 |
| 2009/0138122 A1 * | 5/2009 | Wagner | G06F 19/327 700/226 |
| 2009/0139189 A1 | 6/2009 | Yuyama | |
| 2010/0011715 A1 | 1/2010 | Freudelsperger | |
| 2010/0024662 A1 | 2/2010 | Bengtson et al. | |
| 2010/0042255 A1 * | 2/2010 | Boutin | G07F 11/165 700/242 |
| 2010/0043349 A1 * | 2/2010 | Yuyama | B65B 5/103 53/52 |
| 2010/0232570 A1 * | 9/2010 | Duppre | B65B 57/10 378/57 |
| 2010/0287880 A1 | 11/2010 | Yasunaga | |
| 2011/0202171 A1 * | 8/2011 | Rosenbaum | G06F 19/3462 700/216 |
| 2011/0208352 A1 | 8/2011 | Knoth | |

(56) References Cited

U.S. PATENT DOCUMENTS

| | | | |
|---|---|---|---|
| 2011/0278319 A1* | 11/2011 | Knoth | G06F 19/3462 221/1 |
| 2011/0278329 A1 | 11/2011 | Enns | |
| 2012/0006708 A1* | 1/2012 | Mazur | A61J 7/0481 206/438 |
| 2012/0073241 A1* | 3/2012 | Mahar | G01G 19/4148 53/55 |
| 2012/0259456 A1* | 10/2012 | Saltsov | A61J 7/0076 700/236 |
| 2012/0290129 A1* | 11/2012 | Luciano, Jr. | B65D 75/42 700/244 |
| 2012/0305133 A1 | 12/2012 | Ansaloni et al. | |
| 2012/0330684 A1* | 12/2012 | Jacobs | H04N 7/18 705/3 |
| 2013/0001233 A1 | 1/2013 | Hylton | |
| 2013/0018503 A1* | 1/2013 | Carson | B65B 57/16 700/216 |
| 2013/0142406 A1* | 6/2013 | Lang | G06K 9/6293 382/128 |
| 2013/0218330 A1* | 8/2013 | Chudy | G06F 19/3462 700/244 |
| 2013/0284100 A1 | 10/2013 | Mackelvie | |
| 2013/0318931 A1* | 12/2013 | Holmes | B65B 1/02 53/562 |
| 2013/0340390 A1* | 12/2013 | Carson | B25J 9/0096 53/411 |
| 2014/0033658 A1 | 2/2014 | Habraken et al. | |
| 2014/0096479 A1* | 4/2014 | Pearson | B65B 61/26 53/131.4 |
| 2014/0230376 A1* | 8/2014 | Knoth | B65B 9/045 53/452 |
| 2014/0261881 A1* | 9/2014 | Chudy | A61J 7/0084 141/94 |
| 2015/0239664 A1 | 8/2015 | Liistro et al. | |
| 2015/0290084 A1* | 10/2015 | Kim | A61J 7/0069 221/1 |
| 2015/0352574 A1 | 12/2015 | Kolb | |
| 2016/0007799 A1 | 1/2016 | Steeb | |
| 2016/0009490 A1 | 1/2016 | Scherer | |
| 2016/0104277 A1* | 4/2016 | Takamori | G01J 3/46 382/128 |
| 2016/0122045 A1 | 5/2016 | Kames et al. | |
| 2016/0256639 A1* | 9/2016 | Van Sickle | A61M 15/008 |
| 2017/0015445 A1* | 1/2017 | Holmes | B65B 1/02 |

FOREIGN PATENT DOCUMENTS

| | | |
|---|---|---|
| JP | 5743276 U | 3/1982 |
| JP | 2017533047 | 11/2017 |
| WO | WO 2008/031213 A1 | 3/2008 |
| WO | 2016073360 | 5/2016 |
| WO | 2016073512 | 5/2016 |

OTHER PUBLICATIONS

International Patent Application No. PCT/US2015/058630, International Preliminary Report on Patentability dated May 9, 2017, 6 pages.

International Patent Application No. PCT/US15/58875, International Search Report and Written Opinion dated Mar. 2, 2016, 7 pages.

International Patent Application No. PCT/US2015/058630, International Search Report and Written Opinion dated Jan. 12, 2016, 6 pages.

U.S. Appl. No. 14/533,962, Non-Final Office Action dated Mar. 3, 2017, 10 pages.

EP15856733.9 received an Extended European Search Report dated May 29, 2018, 14 pages.

U.S. Appl. No. 14/533,962, Final Office Action dated Sep. 25, 2017, 25 pages.

U.S. Appl. No. 14/533,962, Advisory Action dated Dec. 26, 2017, 6 pages.

EP15857770.0 received an Extended European Search Report dated Jul. 25, 20108, 12 pages.

U.S. Appl. No. 14/533,962 received a Notice of Allowance dated Sep. 6, 2018, 10 pages.

* cited by examiner

SYSTEMS AND METHODS FOR AUTOMATICALLY VERIFYING PACKAGING OF SOLID PHARMACEUTICALS VIA ROBOTIC TECHNOLOGY ACCORDING TO PATIENT PRESCRIPTION DATA

BACKGROUND OF THE INVENTION

Field of the Invention

The present invention relates generally to the field of automated oral solid pharmaceutical packaging mechanisms for packaging oral solid pharmaceuticals in packages in accordance with patient prescription information. More specifically, the present invention is directed to systems and methods for automatically verifying placement of oral solid pharmaceuticals within packaging according to patient prescription data. A variety of systems and methods are disclosed which provide rapid and efficient verification of oral solid pharmaceutical product placement within packaging in accordance with patient prescription data. The systems and methods which are described below provide multiple independent verifications within a single piece of automation that ensure absolute confidence that the placement of oral solid pharmaceuticals within packaging strictly matches patient prescription dosing information.

Description of the Related Art

Currently, various automated packaging systems exist for placing oral solid pharmaceuticals into packaging solutions which correlate individual dosing times with patient prescription dated. Examples include U.S. Pat. Nos. 8,831,773 and 7,185,476 which are incorporated herein by reference. These issued patents describe systems that are capable of placing one or more oral solid pharmaceutical products into package cavities that correspond to patient prescription data and are herein incorporated by reference in their entirety. While the existing solutions describe various systems that are capable of rapidly and efficiently placing oral solid pharmaceuticals into packages, there remains a need in the art for ensuring that the oral solid pharmaceuticals have been precisely placed into the packages according to the patient prescription data with absolute confidence and within a single system. Currently there are no systems available that provide automatic verification that oral solid pharmaceutical packaging has been filled precisely according to patient prescription data within a single system and blister carded packaging. Accordingly, there remains a need in the field for systems and methods that are capable of ensuring that oral solid pharmaceuticals have been placed strictly in accordance with predetermined patient prescription data within a single system and in blister carded packaging.

The conventional approach to solving this issue requires that a trained technician or pharmacist review the packaged pharmaceuticals in order to ensure that the oral solid pharmaceutical products have been properly placed within the packaging material. The conventional approach is prone to errors and significant delays associated with the manual review process. Applicants' innovation that is set forth below overcomes these deficiencies of existing systems and obviates the need for post packaging quality review. Applicants' unique use and arrangement of various sensors ensures that the oral solid pharmaceuticals have been packaged properly.

SUMMARY OF THE PRESENT INVENTION

In accordance with a first preferred exemplary embodiment of the present invention, robotic pick-and-place automation is used to transfer oral solid pharmaceuticals from moveable trays or canisters that have been quality checked by a pharmacist to package locations in accordance with patient prescription data. Advantageously, in accordance with the present invention, a variety of sensors are used in order to verify that the oral solid pharmaceuticals have been properly placed in the desired oral solid pharmaceutical package locations precisely according to the patient prescription data. In accordance with a first preferred embodiment of the present invention, a pharmacist places oral solid pharmaceutical products within dispensing trays or canisters which are used to present the oral solid pharmaceutical products for picking and placing via the robotic pick-and-place machinery. Once the canister or tray is located adjacent the pick-and-place device, a further sensor or imaging unit associated with the pick-and-place device verifies that the oral solid pharmaceutical product presented by the tray or canister matches the size and shape and/or color of an expected oral solid pharmaceutical product that is to be placed within the packaging material in accordance with patient prescription data that is stored by a computer associated with the system.

If the expected data matches the actual oral solid pharmaceutical product sensed by the imaging unit associated with the pick-and-place device, the robotic pick-and-place continues to transfer one oral solid pharmaceutical product to a desired package location which has a dosing time corresponding to the patient prescription data that is for the package that is currently being filled. Once the robotic pick-and-place end of arm tooling has transferred the oral solid pharmaceutical product to the desired package location, additional sensing units ensure that the transfer is completed into the desired package location in order to verify that the robotic pick-and-place unit has dropped the oral solid pharmaceutical product into a desired package location. If the imaging sensor of the robotic pick-and-place device determines that the oral solid pharmaceutical product presented at the tray or canister is not a match to the expected oral solid pharmaceutical product according to the current patient prescription data, then the system issues an alert to the system operator in order to prevent the erroneous transfer of oral solid pharmaceutical products into the packaging material and will not pick that oral solid pharmaceutical.

In accordance with a preferred exemplary embodiment of the present invention, a med verification tray or transfer sensing unit is located between the end of arm tooling for the robotic pick-and-place mechanism and a oral solid pharmaceutical product package or temporary store having cavity locations corresponding to the cavities of a solid pharmaceutical package that is to be filled by the system. The med verification tray or transfer sensing unit preferably includes a plurality of sensors that operate to confirm transfer from the robotic pick-and-place end of arm tooling into the package cavity location corresponding to the prescription data that is currently being filled by the system. It is preferred that the system is able to ensure that a specific cavity location is being filled by confirming the drop of the oral solid pharmaceutical from the robotic pick-and-place end of arm tooling.

In accordance with a first preferred exemplary embodiment of the present invention, one or more optical sensing units are used to ensure that the oral solid pharmaceutical product that is transferred by the robotic pick-and-place device actually drops into the specific package cavity location that is to be filled by the system. In a first preferred exemplary embodiment, an optical sensor unit includes an emitter that emits a wide beam that at least substantially covers a region above the cavity location that is to be filled. One or more receiving units are located opposite the emitting unit and sense the emitted beam generated by the emitter. An interrupt signal is generated when the one or more receiving units sense that at least a portion of the beam has been interrupted. Because the emitter and receiving unit are preferably individually associated with each package cavity location, it is possible to confirm that an oral solid pharmaceutical has been transferred by the robotic pick-and-place unit from the dispensing tray or canister specifically into a desired oral solid pharmaceutical package cavity location corresponding to the patient prescription data. This technique ensures strict compliance for packaging oral solid pharmaceutical products in accordance with stored patient prescription data. It is also preferred that the sensors of the med verification tray or transfer sensing unit preferably sense any additional breach of the beam immediately after the drop of the oral solid pharmaceutical product in order to ensure that the oral solid pharmaceutical product does not bounce from the desired oral solid pharmaceutical packaging location when the oral solid pharmaceutical product is dropped by the robotic pick-and-place device.

A further verification may also be performed by imaging the packaged pharmaceuticals and matching the oral solid pharmaceutical products located within each package cavity with the corresponding patient prescription data for the specific dosing time corresponding to the package cavity location. In accordance with the foregoing verifications, it is possible to ensure that the individual oral solid pharmaceutical package cavities have been filled with the appropriate doses corresponding to predetermined patient prescription data with absolute confidence. Conventional systems have not been able to provide this high level of confidence for the existing automated oral solid pharmaceutical packaging systems. The present invention overcomes these shortcomings and deficiencies of the existing systems thereby providing a much more economical and efficient packaging solution.

DETAILED DESCRIPTION OF THE PRESENTLY PREFERRED EMBODIMENTS

Figure 1:
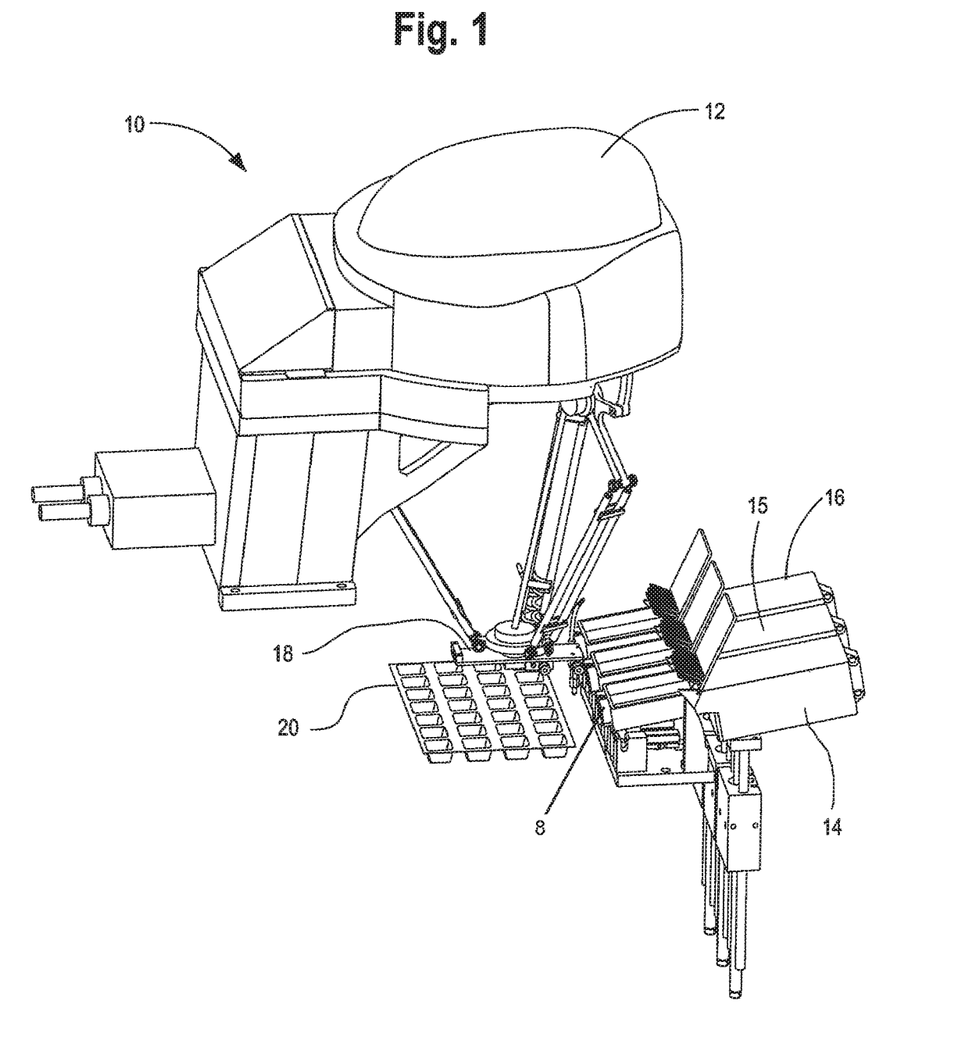
FIG. 1 illustrates a first exemplary embodiment of the overall robotic pick-and-place oral solid pharmaceutical packaging system of the present invention.

FIG. 1 illustrates a first preferred exemplary embodiment of the present invention which is generally shown at 10 in the illustration. A robotic pick-and-place unit 12 transfers oral solid pharmaceutical products from the transfer trays or cassettes 14, 15, 16 into individual oral solid pharmaceutical package locations in accordance with patient prescription data. The individual transfer trays or cassettes 14, 15, 16 are preferably transferred to the respective locations shown in the illustration by another transfer robot from a staging location at which a pharmacist or technician fills the individual trays or cassettes from bulk storage. An initial verification is provided by a pharmacist or technician in order to ensure that the medications placed into the transfer trays or cassettes 14, 15, 16 match the medication designated for a specific transfer tray or cassette. Bar coding verification or other automatically verified visual coding is preferably used by the automated system in order to confirm that an individual tray or cassette that is staged adjacent the robotic pick-and place unit 12 for filling matches the designation provided by the pharmacist or technician at the time of filling.

An additional verification of the oral solid pharmaceutical is performed by an imaging unit (not shown) that is preferably associated with the end of arm tooling portion 18 of the robotic pick-and-place unit 12. The imaging unit provides image data for comparison with a library of image data that is used to ensure the oral solid pharmaceutical actually picked up by the robotic pick-and place unit 12 matches an expected oral solid pharmaceutical designated by a prescription to be filled based on a plurality of visual characteristics including one or more of shape, size, and/or color of the solid oral pharmaceutical. The imaging unit is also preferably used in order to ensure that the end of arm tooling is placed properly above a specific oral solid pharmaceutical so that the suction tip is able to grab and move an individual solid pharmaceutical. An automated processing unit compares the actual image data with expected image data to determine whether there is a match, if there is no match then an alert is issued to the system operator.

Figure 2:
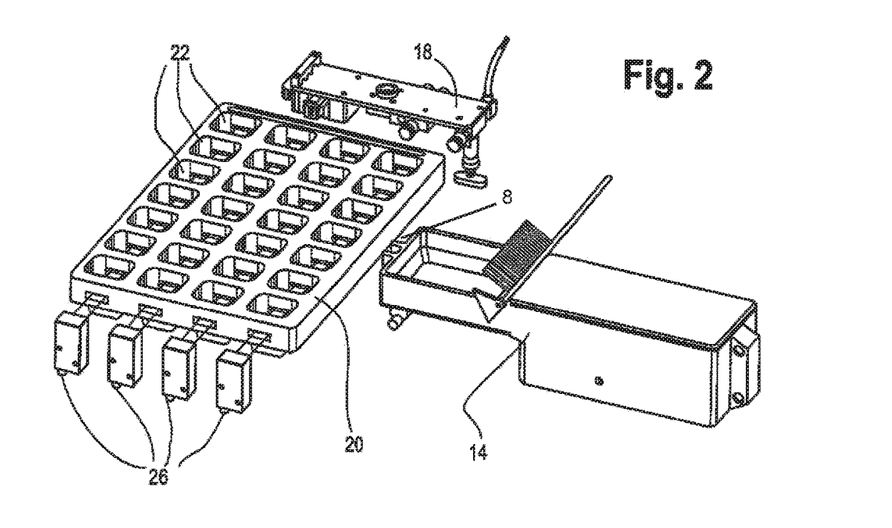
FIG. 2 illustrates a first exemplary embodiment of the med verification tray or transfer sensing unit of the present invention.

In accordance with a preferred exemplary embodiment as illustrated in FIGS. 1 and 2, the end of arm tooling portion 18 initially engages a suction tip 75 that is secured to the transfer tray or cassette 14, 15, or 16 from which a solid oral pharmaceutical 24 is to be transferred for packaging. The suction tip 75 is a soft rubber end that is engaged and removed from the end of arm tooling portion 18 at each cassette 14, 15, or 16 so that each cassette or transfer tray 14, 15, or 16 has its own dedicated suction tip 75 thereby avoiding the potential for cross-contamination from different medications that are filled by the system. Once all medications have been transferred from a particular transfer tray or cassette 14, 15, or 16 for a particular package that is being filled by the system, the suction tip 75 of the end of arm tooling portion 18 is again secured to its corresponding transfer tray or cassette 14, 15, or 16 so that it is available for use the next time that a solid oral pharmaceutical 24 is to be transferred from the transfer tray or cassette 14, 15, or 16. The round suction tip 75 is preferably temporarily secured at the transfer tray or cassette 14, 15, or 16 via a plastic semicircular structure 8 so that the end of arm tooling portion 18 can easily engage and disengage the suction tip 75 of each cassette or transfer tray 14, 15, or 16.

FIG. 1 also illustrates the location of the med transfer verification unit 20 that is placed above a package or package template that is to be filled by the system. The med transfer verification unit 20 incorporates a plurality of sensors that verify the transfer into a specific package or package template cavity corresponding to a patient prescription that is filled by the system.

FIG. 2 illustrates a first exemplary embodiment of the med transfer verification unit 20. The med transfer verification unit 20 preferably includes an array of cavities 22 that each individually provide a transfer path for a solid oral pharmaceutical that is packaged by the system of the present invention. The array of cavities 22 of the med transfer verification unit 20 preferably correspond with the individual cavities of an oral solid pharmaceutical product package that is located beneath the med transfer verification unit 20. Each cavity of the package or package template corresponds with a specific patient dosing time and the system automatically transfers each required oral solid pharmaceutical into its specified location strictly in accordance with predetermined patient prescription data using the robotic pick-and-place unit.

FIG. 2 also illustrates a plurality of electromagnetic emitter units 26 that are used to verify that medication transferred by the robotic pick-and-place unit actually drops into a desired package cavity or template location. In accordance with this first embodiment, an electromagnetic energy receiving unit (not shown) is placed opposite each of the electromagnetic emitting units and a path is formed in the med transfer verification unit 20 through the oral solid pharmaceutical transfer path for each cavity in a given row or column of the med transfer verification unit 20 in order to confirm that an oral solid pharmaceutical has been deposited in a desired cavity according to the predetermined patient prescription data. In accordance with this first embodiment of the med transfer verification unit 20, it is possible to verify that an oral solid pharmaceutical has been deposited by the end of arm tooling but verification is only possible for rows or columns of the med transfer verification unit 20. Those skilled in the art will appreciate that additional emitters and receivers can be used in order to provide greater resolution for pill drop verification into each individual cavity. The med transfer verification unit 20 also acts as a barrier between cavities to prevent inadvertent transfer of the medication between the cavities.

Figure 3:
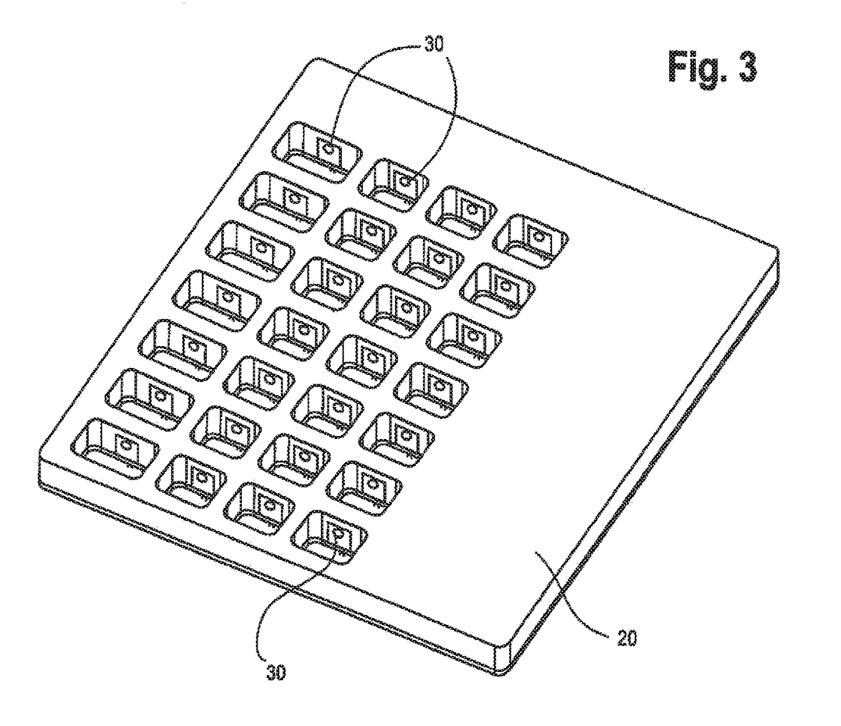
FIG. 3 illustrates a second exemplary embodiment of the med verification tray or transfer sensing unit of the present invention.

FIG. 3 illustrates an alternate embodiment of the med transfer verification unit 20 wherein each cavity 22 of the med transfer verification unit 20 includes its own pair of electromagnet emitter and receiver units for specifically confirming that a solid oral pharmaceutical has been dropped into a specific cavity of a package in accordance with patient prescription data. The electromagnetic emitter units are not shown in the illustration of FIG. 3. FIG. 3 illustrates the med transfer verification unit 20 and the individual electromagnetic receiving units 30 that are individually associated with each cavity of the med transfer verification unit 20. When an individual solid oral pharmaceutical is dropped by the robotic pick-and-place unit through a specific cavity of the med transfer verification unit 20, the med transfer verification unit 20 is able to sense and verify the drop of the solid oral pharmaceutical based on a break in the beam that is received by each of the electromagnetic receiving units 30. This sensing of the drop at each individual cavity provides confirmation that the oral solid pharmaceutical that has been dropped by the robotic pick-and-place unit into the package strictly in accordance with the predetermined patient prescription data. The individual electromagnetic emitters and receivers can also be used to ensure that pills have not bounced out from the cavities by verifying that only a single break in the beam is associated with each pill drop.

Additional image data from optical sensing units positioned above and/or below the package cavity may be used to further confirm that each individual cavity has been properly filled with the oral solid pharmaceuticals strictly in accordance with the predetermined patient prescription data.

Figure 4:
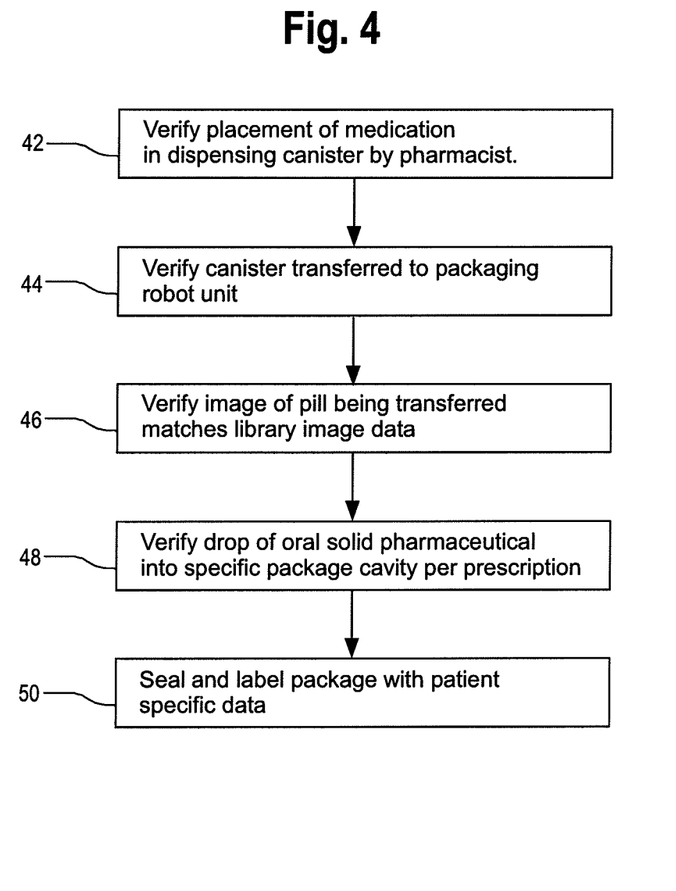
FIG. 4 is a flow diagram illustration of the process for automatically verifying packaging of oral solid pharmaceuticals.

FIG. 4 is a flow diagram which illustrates the overall process for automatically verifying the placement of oral solid pharmaceutical products into specific cavities of a package strictly in accordance with patient prescription data stored in an electronic memory of a computer controller that is used for controlling the packaging machinery. In step 42 a pharmacist or technician verifies transfer of medication from bulk storage into the appropriate canister or dispenser for the specified medication. The medication canister is returned to a carousel where it can be automatically retrieved by a robot for transfer to the robotic pick-and place device of the present invention. It is preferred that a bar code, QR code or rfid reader associated with the system reads a code on the canister before it is positioned at a specific location in a staging area so a robotic retriever can transfer the desired canister automatically to the robotic pick-and-place unit.

In step 44, a bar code or other automated reader reads a code or data from the canister when it is transferred to the staging area of the robotic pick-and-place packaging system in order to ensure that the system transfers the desired medication. In step 46, image data from the pick-and-place unit verifies that the individual pill being transferred has physical characteristics matching those of the expected pill. In step 48, the system verifies drop of the pill into the specific package cavity corresponding to the patient prescription data. Finally, in step 50, the resultant package is labeled and sealed with the patient specific data after all required medications for all doses specified by patient prescription data have been filled by the system into the cavities of the product package.

In an alternate more manual version of the system, the med transfer verification tray includes one or more lights that illuminate at a region of the tray corresponding to a specific cavity of the package that is to be filled with an oral solid pharmaceutical. This assists in the manual transfer of oral solid pharmaceuticals into specific package cavities according to patient prescription data. The remaining operations associated with pill transfer can then be performed in accordance with manual transfer into a package cavity. The system cause one or more lights in a specific region to illuminate in order to guide the user to place a solid pharmaceutical in a desired package location corresponding to patient prescription data.

Figure 5:
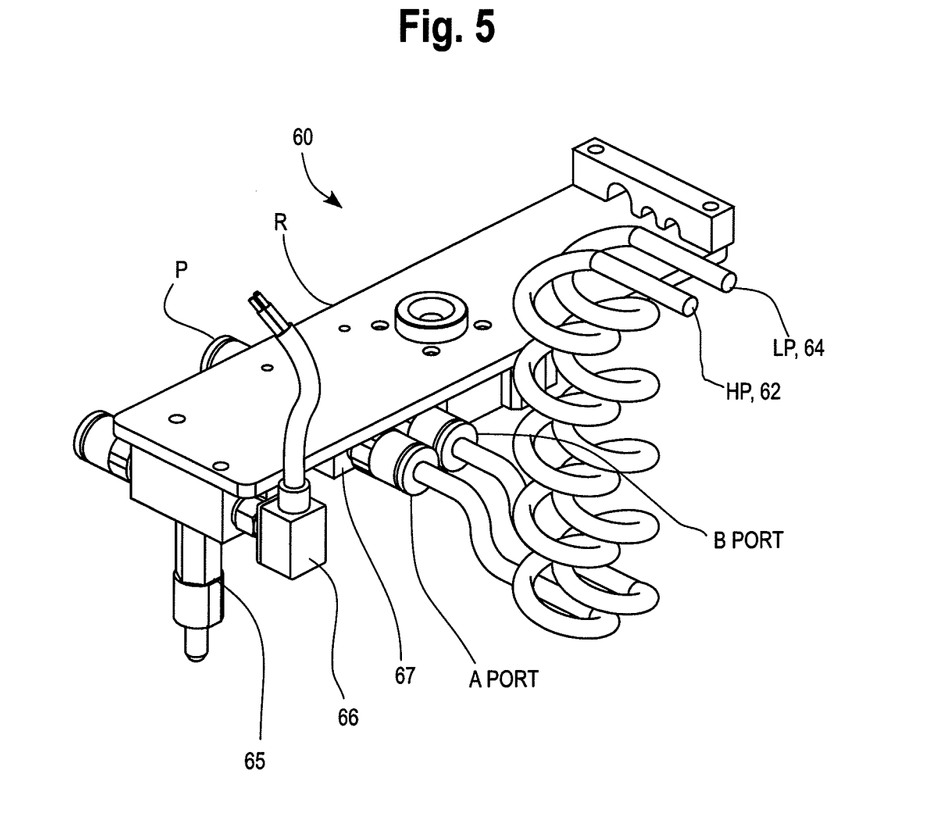
FIG. 5 illustrates a second exemplary embodiment of the oral solid pharmaceutical transfer tray or cassette of the present invention

FIG. 5 illustrates the details of the end of arm tooling for the robotic pick-and-place device which is shown generally at 60. High pressure and low pressure lines 62 and 64 operate to generate a vacuum at the suction tube 65. A pressure sensor 66 located proximate the suction tube 65 operates to ensure that a pill has been picked up by the system based on a predetermined pressure change at the pressure sensor 66. A valve 67 is a pneumatic solenoid switch that selectively applies the vacuum at the suction tube 65. The switch is preferably a 2 msec switch which causes the pressure change within 10 msec at the suction tube end within 10 msec. The solenoid switch or valve 67 consists of four standard ports and the port A and B are the supply of negative pressure and positive pressure. Port A is directly coupled to the vacuum ejector which supplies the negative pressure and port B is directly coupled to a positive pressure regulator which supplies low positive pressure. As a result, the P port is the port which supplies the vacuum pressure and the positive pressure to the suction tube. Ports A and B always have the vacuum and positive pressure active during picking and placing operations. This arrangement assures rapid pressure changes at the end of the suction tube 65. The positive pressure is required to simply and effectively remove the vacuum pressure at the end of suction tube 65.

For performing pill drop verification, it is preferred to use emitters such as model LV S 62 manufactured by Keyence as an optical emitter along with an optical sensor. Alternatively a Fairchild semiconductor infrared emitting diode can be used as the light source in conjunction with an optical sensor. Those skilled in the art will appreciate that virtually any emitter and sensor can be used to sense a break in the sensed emission beam associated with the transit of an oral solid pharmaceutical into a product package cavity. In an alternate arrangement, it is recognized that one or more imaging units could be used to sense the transit of oral solid pharmaceuticals into package cavities but this arrangement requires additional image data processing in order to identify transfer into a specific package cavity.

Those skilled in the art will appreciate that various substitutions and alterations can be made to the systems and methods described in the instant application while still falling within the scope of the appended claims.

We claim:

1. A method for automatically verifying packaging of oral solid pharmaceutical medications comprising:
   verifying placement of a plurality of oral solid pharmaceuticals into each of a plurality of dispensing containers, each individual dispensing container being dedicated to a specific oral solid pharmaceutical medication;
   automatically transferring a plurality of individual dispensing containers to a staging location of a robotic pick-and-place transfer mechanism and verifying that a specific dispensing container is located at a specific staging location for transferring oral solid pharmaceuticals from the dispensing container;
   moving an end of an arm tooling of the robotic pick-and-place transfer mechanism to engage a first suction tip that is removably secured to a first dispensing container associated with a first type of oral solid pharmaceutical;
   using the robotic pick-and-place transfer mechanism to automatically transfer individual oral solid pharmaceutical medications from at least one of a plurality of dispensing containers to cavity locations of a transfer validation unit that each correspond to patient prescription data;
   automatically verifying that each oral solid pharmaceutical medication transferred by the robotic pick-and-place transfer mechanism matches predetermined physical parameters of an oral solid pharmaceutical that is specified for transfer into a specific cavity location based on the patient prescription data;
   detecting a break in a first emitter beam for a single one of the individual oral solid pharmaceutical medications, wherein the emitter beam extends in a generally parallel or generally planar direction relative to the transfer validation unit;
   detecting an additional break in a second emitter beam during transfer of the single one of the individual oral solid pharmaceutical medications;
   determining, based on the detected additional break, that the single one of the individual oral solid pharmaceutical medications was transferred to an incorrect cavity location;
   upon transferring all of the first type of oral solid pharmaceutical for a particular package, securing, using the end of the arm tooling, the first suction tip to the first dispensing container;
   moving the end of the arm tooling of the robotic pick-and-place transfer mechanism to engage a second suction tip that is removably secured to a second dispensing container associated with a second type of oral solid pharmaceutical; and
   automatically sealing and printing patient identification and prescription data on the package once all oral solid pharmaceutical specified by the patient prescription data have been transferred into the package cavities specified by the patient prescription data.

2. The method for automatically verifying packing of oral solid pharmaceutical medications of claim 1, wherein:
   the predetermined physical parameters comprise visual characteristics of the oral solid pharmaceutical stored as image data;
   the predetermined physical parameters are detected using an optical imager; and
   the automatically verifying that each oral solid pharmaceutical medication transferred by the robotic pick-and-place transfer mechanism matches predetermined physical parameters comprises comparing the image data with a library containing a plurality of image data for a plurality of oral solid pharmaceuticals.

3. The method for automatically verifying packing of oral solid pharmaceutical medications of claim 1, wherein:
   each of the cavity locations corresponds to an individual cavity of the package.

4. The method for automatically verifying packing of oral solid pharmaceutical medications of claim 1, wherein:
   the first emitter beam extend between an electromagnetic emitter unit and an electromagnetic energy receiving unit.

5. The method for automatically verifying packing of oral solid pharmaceutical medications of claim 1, wherein:
   the first emitter beam extends across one or both of a row or a column of cavity location of the transfer validation unit.

6. The method for automatically verifying packing of oral solid pharmaceutical medications of claim 1, wherein:
   the first emitter beam extends across a single cavity location.

7. The method for automatically verifying packing of oral solid pharmaceutical medications of claim 1, wherein:
   each cavity location comprises a dedicated emitter beam.

8. The method for automatically verifying packing of oral solid pharmaceutical medications of claim 1, further comprising:
   detecting a second break in the first emitter beam by a second one of the individual solid oral pharmaceutical medications;
   determining that the second break in the first emitter beam is the only break in any of the plurality of emitter beams during transfer of the second one of the individual oral solid pharmaceutical medications.

9. A method for automatically verifying packaging of oral solid pharmaceutical medications comprising:
   moving an end of an arm tooling of a robotic pick-and-place transfer mechanism to engage a first suction tip that is removably secured to a first dispensing container associated with a first type of oral solid pharmaceutical;
   using the robotic pick-and-place transfer mechanism to automatically transfer individual oral solid pharmaceutical medications from at least one of a plurality of dispensing containers to cavity locations of a transfer validation unit that each correspond to patient prescription data;
   verifying, using an optical imaging device, that each oral solid pharmaceutical medication transferred by the robotic pick-and-place transfer mechanism matches predetermined physical parameters of an oral solid pharmaceutical that is specified for transfer into a specific cavity location based on the patient prescription data;

detecting a break in a first emitter beam for a single one of the individual oral solid pharmaceutical medications, wherein the emitter beam extends in a generally parallel or generally planar direction relative to the transfer validation unit;

detecting an additional break in a second emitter beam during transfer of the single one of the individual oral solid pharmaceutical medications;

determining, based on the detected additional break, that the single one of the individual oral solid pharmaceutical medications was transferred to an incorrect cavity location;

upon transferring all of the first type of oral solid pharmaceutical for a particular package, securing, using the end of the arm tooling, the first suction tip to the first dispensing container;

moving the end of the arm tooling of the robotic pick-and-place transfer mechanism to engage a second suction tip that is removably secured to a second dispensing container associated with a second type of oral solid pharmaceutical; and automatically sealing and printing patient identification and prescription data on the package once all oral solid pharmaceutical specified by the patient prescription data have been transferred into the package cavities specified by the patient prescription data.

10. The method for automatically verifying packing of oral solid pharmaceutical medications of claim 9, wherein:
the first emitter beam extends across one or both of a row or a column of cavity location of the transfer validation unit.

11. The method for automatically verifying packing of oral solid pharmaceutical medications of claim 9, wherein:
each cavity location comprises a dedicated emitter beam.

12. The method for automatically verifying packing of oral solid pharmaceutical medications of claim 9, further comprising:
detecting a second break in the first emitter beam by a second one of the individual solid oral pharmaceutical medications;
determining that the second break in the first emitter beam is the only break in any of the plurality of emitter beams during transfer of the second one of the individual oral solid pharmaceutical medications.

13. A system for automatically verifying packing of oral solid pharmaceutical medications, comprising:
a robotic pick-and-place unit having an arm tooling having an end, wherein the end of the arm tooling is configured to:
move to engage a first suction tip that is removably secured to a first dispensing container associated with a first type of oral solid pharmaceutical;
upon transferring all of the first type of oral solid pharmaceutical for a particular package, secure the first suction tip to the first dispensing container;
move to engage a second suction tip that is removably secured to a second dispensing container associated with a second type of oral solid pharmaceutical;
move between each of a plurality of dispensing containers and cavity location of a transfer validation unit to automatically transfer individual oral solid pharmaceutical medications from at least one of the plurality of dispensing containers to cavity locations of the transfer validation unit that each correspond to patient prescription data, the robotic pick-and-place unit comprising at least one optical imaging device that is configured to:
verify that each oral solid pharmaceutical medication transferred by the robotic pick-and-place transfer mechanism matches predetermined physical parameters of an oral solid pharmaceutical that is specified for transfer into a specific cavity location based on the patient prescription data; and
the transfer validation unit comprising at least one emitter beam configured to:
detect a break in a first emitter beam for a single one of the individual solid oral pharmaceutical medications, wherein the first emitter beam extends in a generally parallel or generally planar direction relative to the transfer validation unit;
detect an additional break in a second emitter beam during transfer of the single one of the individual oral solid pharmaceutical medications; and
determine, based on the detected additional break, that the single one of the individual oral solid pharmaceutical medications was transferred to an incorrect cavity location.

14. The system for automatically verifying packing of oral solid pharmaceutical medications of claim 13, wherein:
the first emitter beam extends across one or both of a row or a column of cavity location of the transfer validation unit.

15. The system for automatically verifying packing of oral solid pharmaceutical medications of claim 13, wherein:
each cavity location comprises a dedicated emitter beam.

16. The system for automatically verifying packing of oral solid pharmaceutical medications of claim 13, wherein:
the transfer validation unit is further configured to:
detect a second break in the first emitter beam by a second one of the individual solid oral pharmaceutical medications; and
determine that the second break in the first emitter beam is the only break in any of the plurality of emitter beams during transfer of the second one of the individual oral solid pharmaceutical medications.

* * * * *